United States Patent
Foley et al.

(10) Patent No.: US 10,405,748 B2
(45) Date of Patent: Sep. 10, 2019

(54) FILAMENT DEVICE AND CORRESPONDING MANUFACTURING METHODS

(71) Applicant: Medline Industries, Inc, Northfield, IL (US)

(72) Inventors: Brian Foley, Northbrook, IL (US); Ben Duck, McHenry, IL (US)

(73) Assignee: Medline Industries, Inc., Northfield, IL (US)

( * ) Notice: Subject to any disclaimer, the term of this patent is extended or adjusted under 35 U.S.C. 154(b) by 108 days.

(21) Appl. No.: 15/670,940

(22) Filed: Aug. 7, 2017

(65) Prior Publication Data
US 2019/0038134 A1    Feb. 7, 2019

(51) Int. Cl.
*A61B 5/00* (2006.01)
*B32B 37/18* (2006.01)

(52) U.S. Cl.
CPC .......... *A61B 5/0053* (2013.01); *A61B 5/4029* (2013.01); *A61B 5/4827* (2013.01); *A61B 5/4005* (2013.01); *B32B 37/18* (2013.01)

(58) Field of Classification Search
CPC ... A61B 5/0053; A61B 5/4029; A61B 5/4827; A61B 5/4005; B32B 37/18
See application file for complete search history.

(56) References Cited

U.S. PATENT DOCUMENTS

| | | | | |
|---|---|---|---|---|
| 3,070,280 A | * | 12/1962 | Richmond | B65D 27/16 229/80 |
| 4,986,289 A | * | 1/1991 | McWhorter | A61C 15/043 132/323 |
| 5,823,969 A | | 10/1998 | Christy | |
| 6,113,551 A | * | 9/2000 | Isaacs | A61B 5/0053 600/557 |
| 6,790,304 B2 | * | 9/2004 | Fox | A61B 5/4827 156/201 |
| D707,828 S | | 6/2014 | Ehninger et al. | |
| D709,205 S | | 7/2014 | Ehninger et al. | |
| D773,058 S | | 11/2016 | Takizawa et al. | |

(Continued)

OTHER PUBLICATIONS

"Disposable Monofilaments", Disposable Monofilaments by AliMed; Published in Medline Catalog; https://www.medline.com/catalog/catalog.jsp; Unknown publication date but prior to filing of present application.

(Continued)

*Primary Examiner* — Eric J Messersmith
(74) *Attorney, Agent, or Firm* — Philip H. Burrus, IV

(57) ABSTRACT

A device (901) is manufactured from a sheet layer (100) defining a plurality of panels (101,102,103). Each panel is connected to at least one other panel along a common edge (104). A perforation (105) extends along the common edge and defines a separation location allowing the each panel to be separated from adjoining panels when an applied force pulls each panel away from the adjoining panels. A score line (115) bisects each panel and is oriented orthogonally with the perforation. The score line allows a first portion (116) of each panel to fold about the score line to abut a second portion (117) of each panel. An adhesive (501), disposed along the first portion, retains the first portion to the second portion, as well as retains the filament between the first portion and the second portion.

20 Claims, 13 Drawing Sheets

(56) References Cited

U.S. PATENT DOCUMENTS

D829,917 S     10/2018  Duck et al.
2009/0014025 A1*  1/2009  Lyulyev ................ A61C 15/04
                                                    132/324

OTHER PUBLICATIONS

"Medline Monofilaments", Medline Monofilaments; Published in Medline Catalog; https://www.medline.com/catalog/catalog.jsp; Unknown Publication date but prior to filing of present applicati.
Davis, Antoine D., "Notice of Allowance", U.S. Appl. No. 29/613,086, filed Aug. 7, 2017; dated Jan. 29, 2019.

* cited by examiner

FILAMENT DEVICE AND CORRESPONDING MANUFACTURING METHODS

BACKGROUND

Technical Field

This disclosure relates generally to devices, and more particularly to medical devices.

Background Art

Medical professionals sometimes require confirmation when a patient claims to have lost sensation in a body part. For example, a diabetic may be suffering from symptoms that include some partial sensation loss in the foot. To confirm whether this is the case, the medical professional will stimulate the skin at various locations, asking the patient whether they can feel the stimulus. A common way to do this is to press the end of a monofilament having a predefined deflection resistance against the skin.

Since the filament has a predefined deflection resistance, the medical professional can continue to press the filament into the skin until it bends. When it bends the medical professional knows that a predefined amount of force has been applied to the skin. In many tests, this amount of force is standardized to an amount such as 10 grams of force in common diabetic tests.

Most prior art filament tests are large, bulky, and unwieldy devices. It would be advantageous to have an improved device with which to conduct filament tests.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

Figure 1:
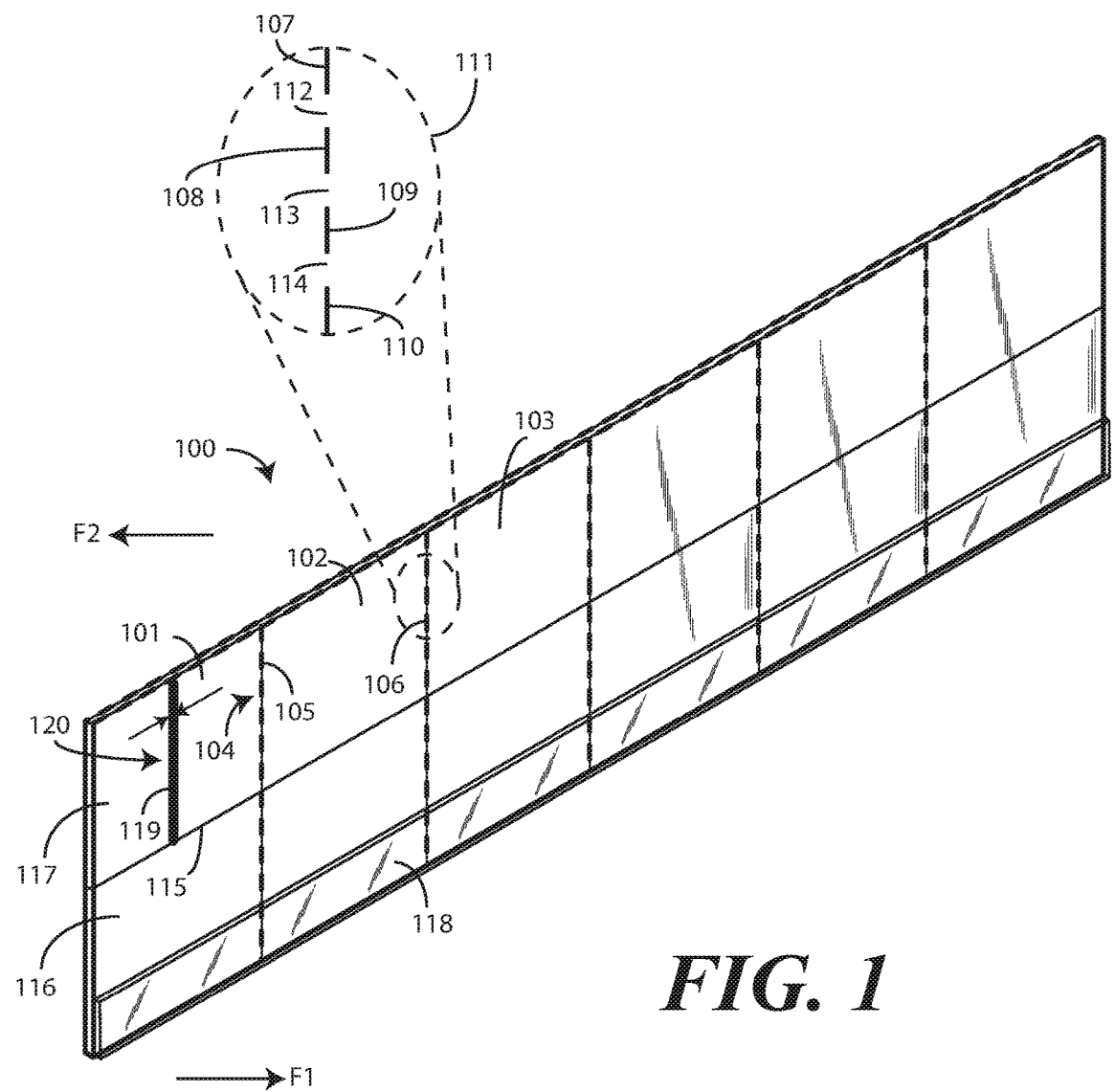
FIG. 1 illustrates a perspective view of one explanatory sheet layer in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions.

As used herein, components may be "coupled" when information can be sent between such components, even though there may be one or more intermediate or intervening components between, or along the connection path. The terms "substantially" and "about" are used to refer to dimensions, orientations, or alignments inclusive of manufacturing tolerances. Thus, a "substantially orthogonal" angle with a manufacturing tolerance of plus or minus two degrees would include all angles between 88 and 92, inclusive. Also, reference designators shown herein in parenthesis indicate components shown in a figure other than the one in discussion. For example, talking about a device (10) while discussing figure A would refer to an element, 10, shown in figure other than figure A.

Embodiments of the disclosure provide a new and improved filament testing device that is easier and quicker to manufacture, thereby saving cost. Rather than having to cut handle portions individually, in one or more embodiments a sheet layer defines a plurality of panels, each of which can be used as a handle for a filament testing device.

In one or more embodiments, each panel of the sheet layer joins at least one other panel at a common edge. A perforation extends along the common edge. The perforation defines a separation location between adjacent panels. This separation location allows each panel to be separated from adjoining panels by tearing along the perforation. Said differently, in one or more embodiments each panel can be separated from adjoining panels by applying a force that pulls the panel away from neighboring panels.

In one or more embodiments, a score line passes across each panel. The score line is oriented orthogonally with at least one of the perforations. The score line, which constitutes a partial incision in the sheet layer, bisects each panel in one or more embodiments. The score line allows a first portion of each panel to fold about the score line to abut against a second portion of the panel.

An adhesive is disposed along either the first portion or the second portion in one or more embodiments. A cover layer can be placed atop the adhesive to prevent the adhesive from being exposed until the cover layer is removed.

To construct filament test devices, in one or more embodiments a filament is placed against each panel. For example, in one embodiment the filament is placed such that it begins at the score line and then extends across, and distally away from, the second panel. To aid in alignment, an aligner can be disposed on the second portion.

Once the filament is placed, the cover layer (if present) is removed from the adhesive, thereby exposing the same. The first portion is then folded about the score line to abut the second portion. The first portion can be pressed against the second portion. This does two things: First, it adhesively retains the second portion to the first portion. Second, it engages the filament, thereby retaining the filament in the handle defined by the first portion and the second portion when adhesively retained together.

Figure 2:
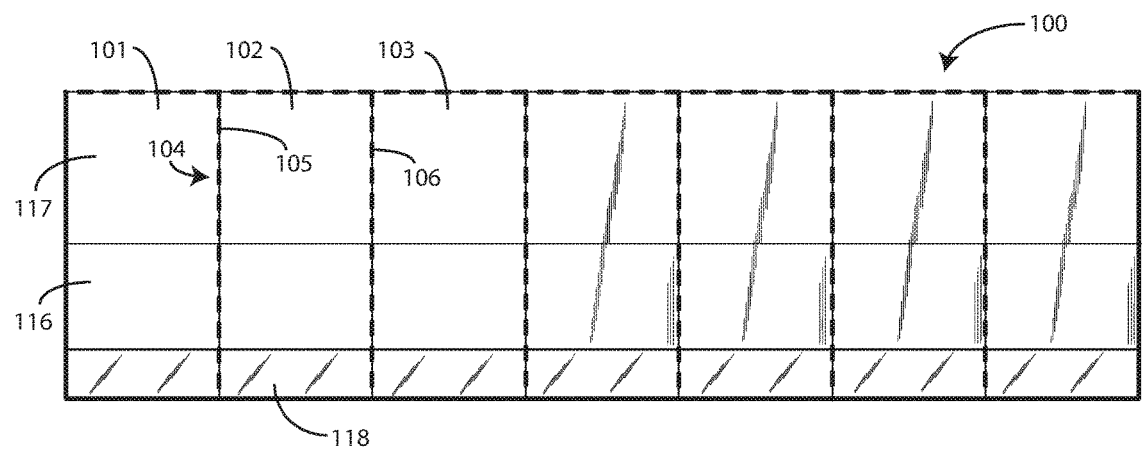
FIG. 2 illustrates a front elevation view of one explanatory sheet layer in accordance with one or more embodiments of the disclosure.
Figure 3:
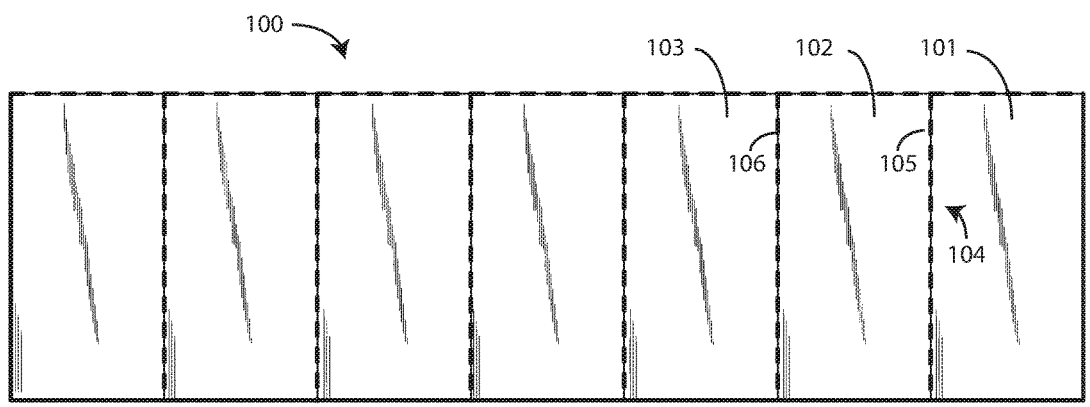
FIG. 3 illustrates a rear elevation view of one explanatory sheet layer in accordance with one or more embodiments of the disclosure.

Turning now to FIGS. 1-3, illustrated therein is one explanatory sheet layer 100 configured in accordance with one or more embodiments of the disclosure. FIG. 1 illustrates a perspective view of the sheet layer 100, while FIGS. 2 and 3 are front elevation and rear elevations of the same, respectively. In one or more embodiments, the sheet layer 100 is manufactured from a paper-based material, such as stock paper, paperboard, cardboard, or baseboard. In other embodiments, the sheet layer 100 is manufactured from a thermoplastic material, such as polyester, polyethylene, polypropylene, nylon, or composite materials. Other materials suitable for manufacturing the sheet layer 100 will be obvious to those of ordinary skill in the art having the benefit if the disclosure. The sheet layer 100 can have printing thereon, such as use instructions and/or branding information.

In one or more embodiments, the sheet layer 100 defines one or more panels 101,102,103. In one or more embodiments, each panel 101 is connected to at least one other panel 102 along a common edge 104. In one or more embodiments, a perforation 105 extends along the common edge 104, thereby defining a separation location between each panel 101,102,103 to facilitate separation of the panel 101 from the adjoining panel 102 or panels. Illustrating by example, panel 102 could be separated from panel 101 and panel 103 via perforations 105,106.

Each perforation 105,106 comprises a series of scores or cuts through the sheet layer 100, while leaving interspaced portions of the sheet layer 100 intact. Each perforation 105,106 allows panels to be separated from adjacent panels when an applied force pulls the panel away from its adjacent panels. Illustrating by example, applying a force to panel 101 to the right and out of the page, as viewed in FIG. 1, while retaining panel 102 in its location, or alternatively applying another force to panel 102 to the left and into the page would cause panel 101 to separate from panel 102 in one or more embodiments.

In one or more embodiments, each perforation 105,106 comprises a score line that allows the sheet layer 100 to more easily be torn. Said differently, in one embodiment the perforation 105,106 is configured to tear and/or split when the one panel 101 is pulled away from an adjoining panel 102. This will be shown in more detail in subsequent figures. When this occurs, the tearing of the perforations 105,106 results in a splitting of the sheet layer 100. The splitting or tearing can cause the panels 101,102 to separate at the common edge 104. Panels can therefore be separated from the sheet layer 100 simply tearing the desired panel away from the sheet layer 100.

In one embodiment, the perforation 106 comprises a plurality of scores 107,108,109,110, as shown in the magnified perforation view 111. Each of the scores 107,108,109, 110 may completely sever the sheet layer 100 in one embodiment. Accordingly, in an embodiment where the scores 107,108,109,110 completely sever the sheet layer 100, they each comprise cuts. In other embodiments, the scores 107,108,109,110 only partially cut into the sheet layer 100. Accordingly, in an embodiment where the scores 107, 108,109,110 only partially sever the sheet layer 100, they each comprise partial incisions.

In one or more embodiments, each of the scores 107,108, 109,110 through, or optionally partially through, the sheet layer 100 is separated by a corresponding length 112,113, 114 of the sheet layer 100. The lengths of the scores 107,108,109,110 and the interspaced lengths 112,113,114 of the sheet layer 100 can vary. In one embodiment, the scores 107,108,109,110 and the interspaced lengths 112,113,114 of the sheet layer 100 are equal in length, with each score 107 being as long as its adjacent length 112 of the sheet layer 100. In another embodiment, the scores 107,108,109,110 are longer than the interspaced lengths 112,113,114 of the sheet layer 100. In still another embodiment, the scores 107,108, 109,110 are shorter than the interspaced lengths 112,113,114 of the sheet layer 100.

In one or more embodiments, a score line 115 defines a partial incision into the sheet layer 100. In the illustrative embodiment of FIGS. 1-3, the score line 115 bisects each panel 101,102,103 and is oriented substantially orthogonally with the perforations 105,106. For example, in this illustrative embodiment the score line 115 bisects panel 101 into a first portion 116 and a second portion 117. Since the score line 115 extends entirely across a width of the sheet layer 100 in this embodiment, the score line 115 also bisects the second panel 102, as well as every other panel of the sheet layer 100.

In this illustrative embodiment, the first portion 116 and the second portion 117 are rectangular in shape. However, where the score line 115 is not a straight line, but is rather curved, piecewise linear, or takes other shapes, the first portion 116 and the second portion 117 of each panel 101,102,103 can take other shapes as well.

In one embodiment, the first portion 116 and the second portion 117 have substantially an equal area, and are thus substantially equal in size. In another embodiment, the first portion 116 is greater in size than the second portion 117. In still another embodiment, the first portion 116 is smaller in size than the second portion 117. In this illustrative embodiment, the score line 115 bisects each of the panels 101,102, 103 into a first portion and a second portion due to the fact that the score line 115 passes across a width of the sheet layer 100.

Figure 7:
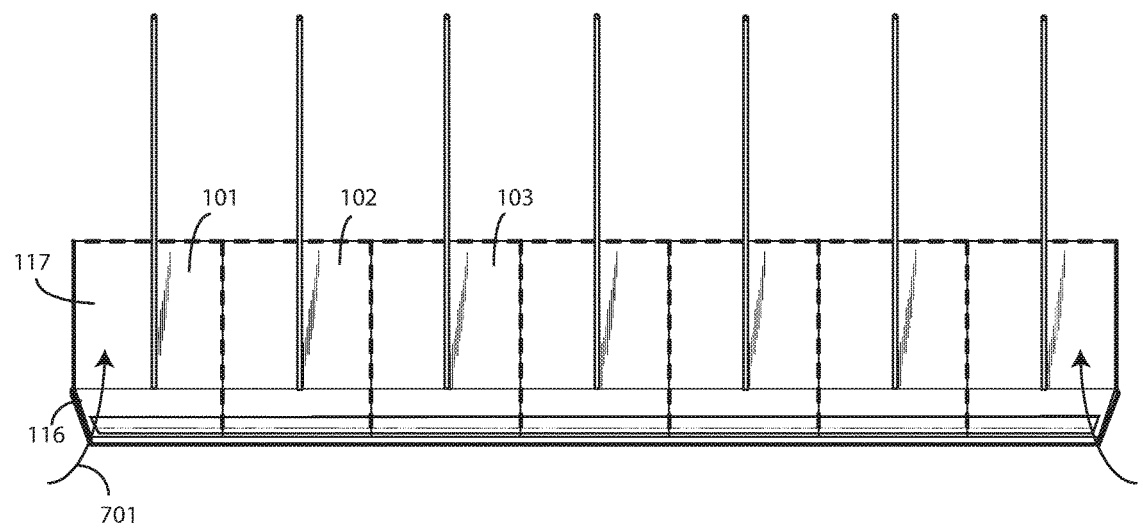
FIG. 7 illustrates one or more method steps in accordance with one or more embodiments of the disclosure.

As will be shown in more detail below with reference to FIG. 7, in one or more embodiments the score line 115 allows the first portion 116 of each panel 101,102,103 to fold about the score line 115. When the first portion 116 of each panel 101,102,103 is fully folded about the score line 115, it will have a major face that abuts another major face of the second portion 117. Accordingly, in one or more embodiments folding the first portion 116 about the score line 115 results in the first portion 116 abutting the second portion 117.

In one or more embodiments, and adhesive is disposed along the first portion 116 of each panel 101,102,103. In the embodiment of FIGS. 1-3, the adhesive (shown in FIG. 6) is disposed beneath a cover layer 118. The cover layer 118 is applied over the adhesive, and is removable to expose the adhesive. In one or more embodiments, this removal of the cover layer 118 occurs prior to any folding of the first portion 116 and/or the second portion 117 about the score line 115.

Figure 8:
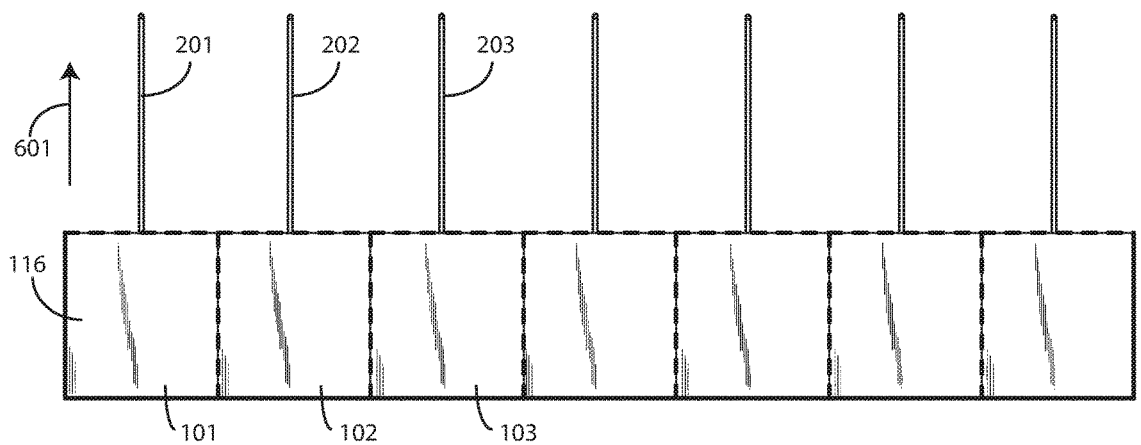
FIG. 8 illustrates one explanatory assembly in accordance with one or more embodiments of the disclosure.

In one or more embodiments, the adhesive comprises is a layer of adhesive tape or applied adhesive material having a height that is less than the height of the first portion 116 of each panel 101,102,103. The cover layer 118 comprises a releasable covering. As will be described in more detail below, when making a testing tool using the panels 101, 102,103 of the sheet layer 100, the cover layer 118 can be removed to reveal the adhesive material. Pressing the first portion 116 against the second portion 117, after folding the former about the score line 115, causes the first portion 116 to be retained against the second portion 117 when the first portion 116 and the second portion 117 abut (as shown in FIG. 8).

In one or more embodiments, each panel 101,102,103 can include an aligner 119. As will be described in more detail below with reference to FIG. 4, in one or more embodiments a filament is placed on each panel 101,102,103 during assembly. To ensure that the filament is placed correctly, in one or more embodiments the second portion 117 of each panel includes an aligner 119. In this illustrative embodiment, the aligner 119 is centrally disposed along the second portion 117.

In this embodiment, the aligner 119 comprises a line and a pair of arrows indicating a predefined location 120 for the filament. In other embodiments, the aligner 119 may be a dashed line or a rectangle indicating the predefined location 120 for the filament. Other types of aligners 119 will be obvious to those of ordinary skill in the art having the benefit of this disclosure.

Figure 4:
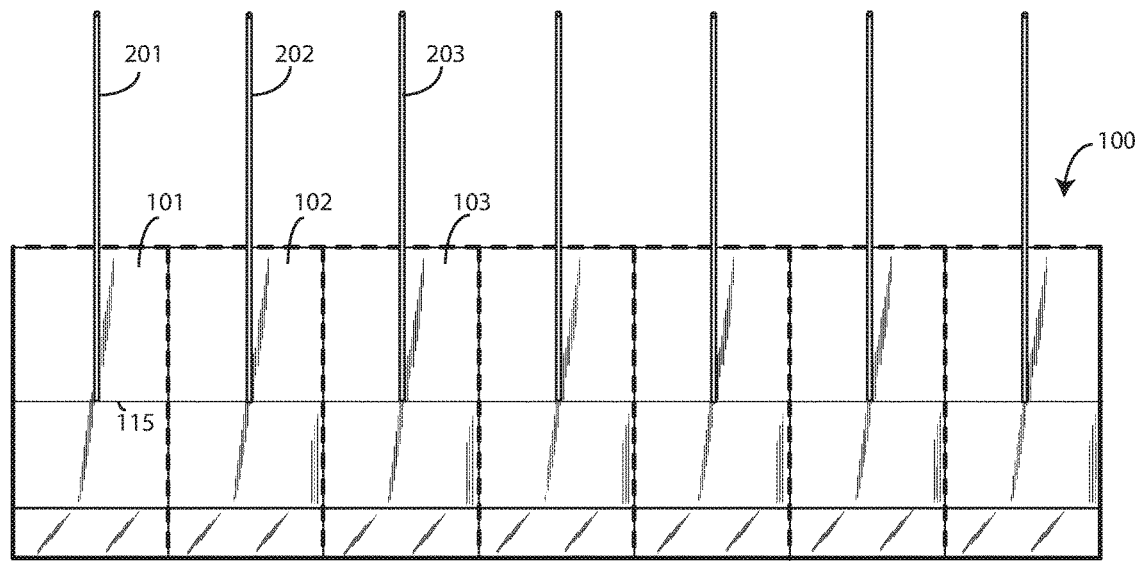
FIG. 4 illustrates one explanatory partial assembly in accordance with one or more embodiments of the disclosure.

Turning now to FIG. 4, illustrated therein is the sheet layer 100 of FIG. 1. As shown, a filament 201,202,203 has been placed on each panel 101,102,103. In this illustrative embodiment, the filament 201,202,203 is situated along the second portion 117 of each panel 101,102,103. In this illustrative embodiment, the filament 201,202,203 extends from the score line 115 initially across the second portion 117 of the each panel 101,102,103.

In one or more embodiments, each filament 201,202,203 is a plastic filament. In other embodiments, each filament 201,202,203 is a nylon filament. Each filament 201,202,203 can have a predefined length, such as between two and two and one half inches. In one or more embodiments, each filament 201,202,203 has a diameter of about 0.0175 inches, although other diameters and lengths will be obvious to those of ordinary skill in the art having the benefit of this disclosure.

As will be illustrated in more detail below, in one or more embodiments when a testing device is constructed, the filament 201,202,203 will be disposed between the first portion 116 and the second portion 117 of each panel 101,102,103 when the first portion 116 is folded toward the second portion 117 about the score line 115. Accordingly, in one or more embodiments the filament 201,202,203 is positioned such that its base is aligned with the score line 115. As such, each filament 201,202,203 extends from the score line initially across, and then distally away from, the second portion 117. As will be shown below with reference to FIG. 8, when the first portion 116 is folded toward the second portion 117 about the score line 115, this placement of the filament 201,202,203 causes the filament 201,202,203 to extend from the score line initially across, and then distally away from, both the first portion 116 and the second portion 117 of each panel 101,102,103.

Figure 5:
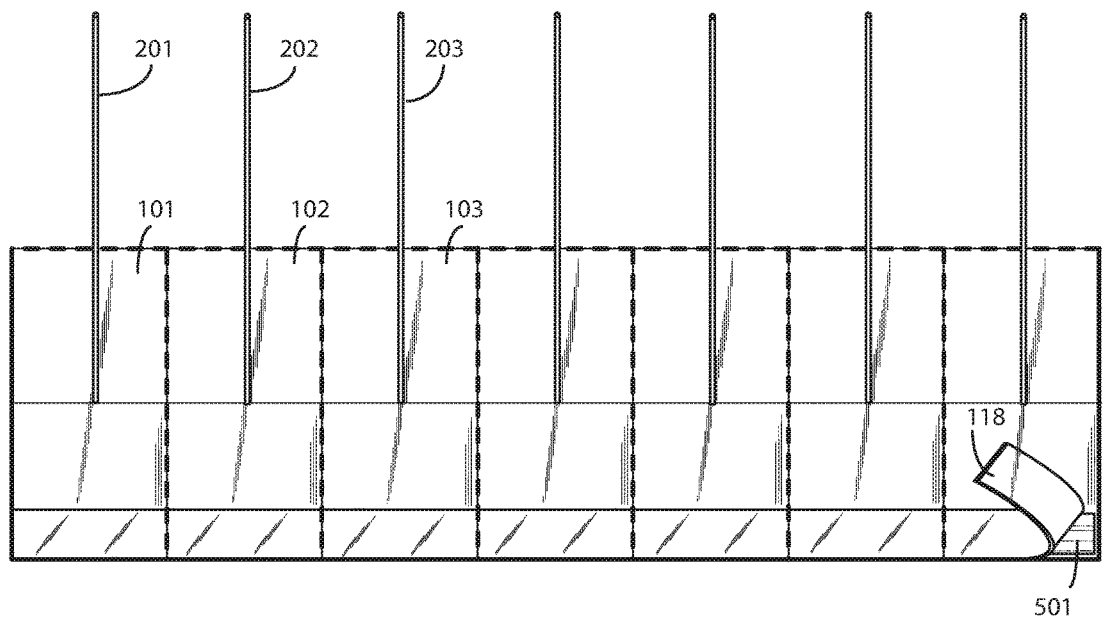
FIG. 5 illustrates one or more method steps in accordance with one or more embodiments of the disclosure.
Figure 6:
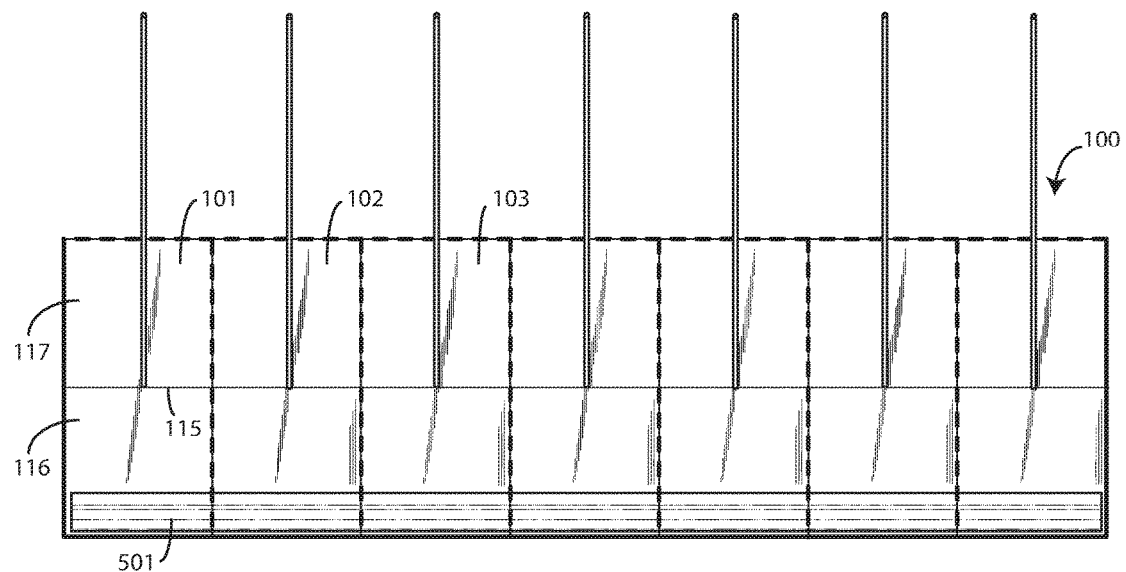
FIG. 6 illustrates another partial assembly in accordance with one or more embodiments of the disclosure.

Turning now to FIG. 5, once each filament 201,202,203 has been placed on each panel 101,102,103, the cover layer 118 applied over the adhesive 501 can be removed, thereby exposing the adhesive 501. Turning now to FIG. 6, once the cover layer (118) is completely removed, the adhesive 501 becomes fully exposed. In one or more embodiments, the adhesive 501 spans a width of the sheet layer 100.

As noted above, in one or more embodiments, the score line 115 allows the first portion 116 of each panel 101,102, 103 to fold about the score line 115 to abut the second portion 117 of each panel 101,102,103. Turning now to FIG. 7, the first portion 116 of each panel 101,102,103 is then folded 701 about the score line 115 toward the second portion 117 of each panel 101,102,103. This folding 701 continues until a major face of the first portion 116 of each panel 101,102,103 abuts a major face of the second portion 117 of each panel 101,102,103, as shown in FIG. 8.

Turning now to FIG. 8, pressing the first portion 116 of each panel 101,102,103 against the abutting major face of the second portion (117) of each panel 101,102,103 causes the adhesive (501) to retain the first portion 116 to the second portion (117) when the first portion 116 and the second portion (117) abut. Since the filament 201,202,203 is disposed between the first portion 116 and the second portion (117) of each panel as shown in FIG. 8, the adhesive (501) also retains the filament 201,202,203 between the first portion 116 and the second portion (117) of each panel 101,102,103.

Since the filament 201,202,203 was placed with an end aligned with the score line (115) as described above with reference to FIG. 6, this results in the filament 201,202,203 extending initially from the score line (115), then across the first portion 116 and the second portion (117), and distally away 801 from the first portion 116 and the second portion (117). In one or more embodiments, the filament 201,202, 203 extends distally away 801 from the first portion 116 and the second portion (117) by a distance of between one and two inches. As shown in FIG. 8, due to the pressure that was applied between the first portion 116 and the second portion (117) of each panel 101,102,103 after the folding of FIG. 7, the adhesive (501) retains the filament 201,202,203 against the second portion (117), as well as the first portion 116, when the first portion 116 and the second portion (117) abut.

Figure 9:
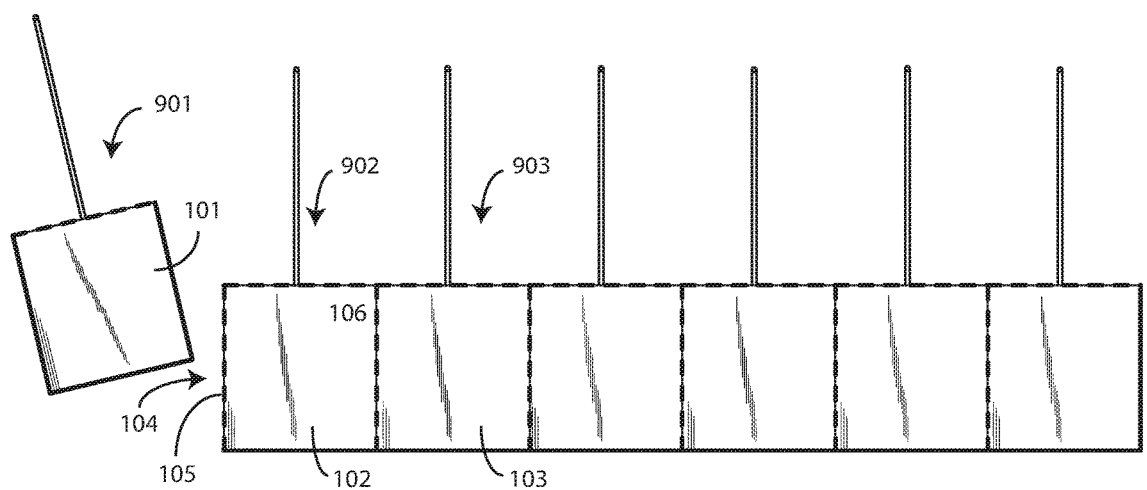
FIG. 9 illustrates a device being detached from one explanatory assembly in accordance with one or more embodiments of the disclosure.
Figure 10:
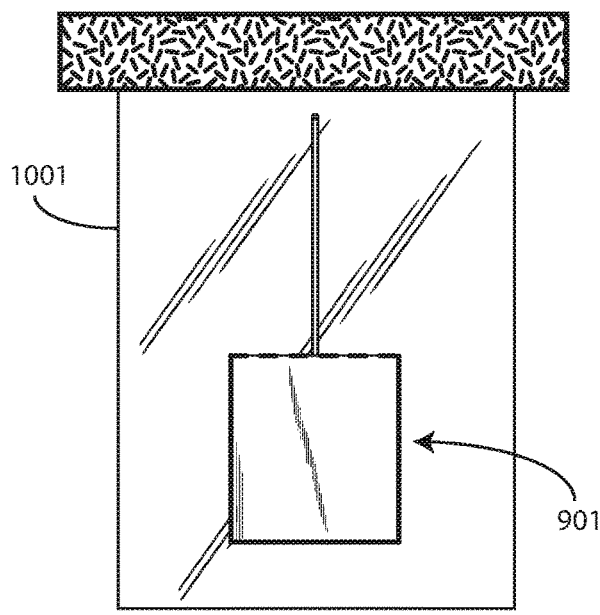
FIG. 10 illustrates on explanatory device in accordance with one or more embodiments of the disclosure.

Turning now to FIG. 9, each completed device 901 can be separated from adjoining devices 902 by tearing the perforation 105 defining the separation location 104 between the panels associated with each device. Illustrating by example, device 901 can be separated from device 902 by applying a force that pulls the first panel 101 from the second panel 102, thereby tearing the perforation 105. Similarly, device 902 can be separated from device 903 by applying a force that pulls the second panel 102 from the third panel 102, and so forth. Once each device 901,902,903 has been separated from adjoining devices, it can be packaged. Turning now to FIG. 10, device 901 has been placed into a package 1001 for shipment to a medical services provider.

Figure 11:
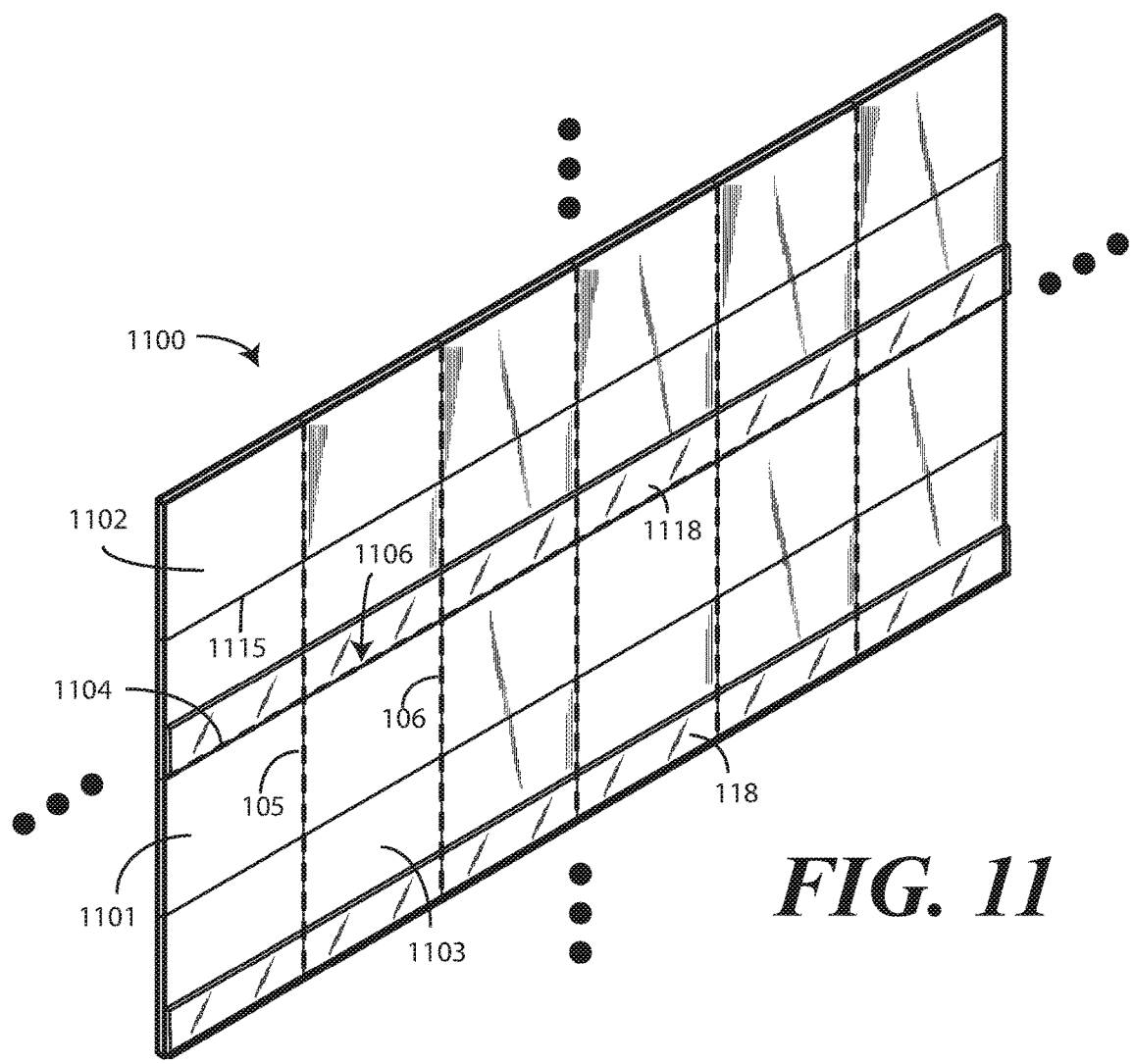
FIG. 11 illustrates another explanatory sheet in accordance with one or more embodiments of the disclosure.

For ease of illustration, the sheet layer (100) described with reference to FIGS. 1-9 was a single row, with the single row including seven panels. However, embodiments of the disclosure are not so limited. Embodiments of the disclosure contemplate that the sheet layer can be extended both in width and in length. Turning now to FIG. 11, illustrated therein is one such sheet layer 1100.

The sheet layer 1100 of FIG. 11 has been expanded in length to illustrate how adjoining panels can be stacked in not only rows, but columns as well. For example, each panel 1101 in FIG. 11 is coupled to at least two other panels 1102,1103 due to this combination of columns and rows. Since the panels 1101,1102,1103 are arranged in columns and rows, in addition to the perforations 105,106 that allow panels 1101,1103 in each row to be separated, another perforation 1104 is oriented orthogonally with these perforations 105,106. This results in a first panel 1101, a second panel 1102, and a third panel 1103 connecting at an intersection 1106 of perforations 105,106 and the other perforation 1104.

This additional perforation 1105 allows panels 1101,1102 or rows of panels 1101,1103 to be separated. In one or more embodiments, rows of panels 1101,1103 are separated from the sheet layer 1100. Then the steps described above with reference to FIGS. 4-9 can be performed on each row to manufacture devices (901,902,903) configured in accordance with embodiments of the disclosure.

While only two rows are shown in FIG. 11 for illustration, embodiments of the disclosure contemplate that more rows can be attached above and below these, with the sheet layer 1100 being then spooled so that rows can be torn along perforation 1105 as needed. Alternatively, a sheet layer without the perforations 105,106,1104 or score lines 115, 1115 could be spooled and fed into automated equipment that applies the perforations 105,106,1104, the score lines 115,1115, the adhesive (501) and the cover layer 118,1118 atop the adhesive (501) as well. Rows of panels can then be dispensed from the spool as needed.

Figure 12:
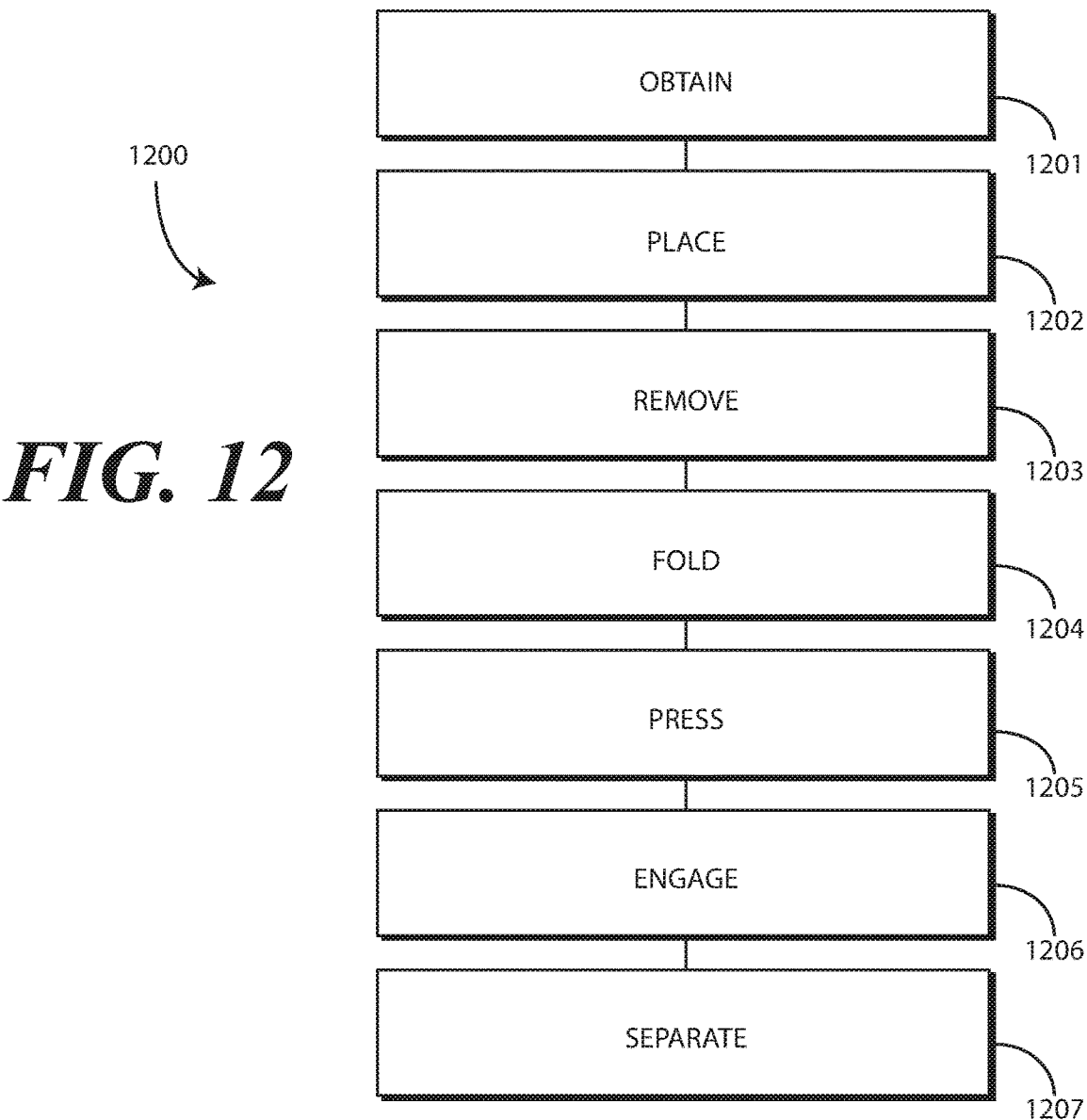
FIG. 12 illustrates one explanatory method in accordance with one or more embodiments of the disclosure.

Turning now to FIG. 12, illustrated therein is one explanatory method 1200 of manufacturing a device in accordance with one or more embodiments of the disclosure. At step 1201, the method 1200 includes obtaining a sheet layer. In one embodiment, the sheet layer defines a plurality of panels. In one embodiment, each panel is connected to at least one other panel along a common edge. In one embodiment, a perforation extends along the common edge. Where included, the perforation defines a separation location between each panel and its adjoining panels.

At step 1202, the method 1200 includes placing a filament along a first portion of the each panel. In one or more embodiments, the first portion comprises an aligner indicating a predefined location for the filament. Where this is true, step 1202 can include placing the filament on the aligner.

At optional step 1203, the method 1200 includes removing a cover layer from an adhesive disposed along a portion of each panel. At step 1204, the method 1200 includes folding a second portion of the each panel about a score line bisecting the each panel and oriented orthogonally with the perforation to cause the first portion of the each panel and the second portion of the each panel to abut.

At step 1205, the method includes pressing the first portion of each panel against the second portion of each panel. In one or more embodiments, this pressing causes an adhesive attached to the second portion of the each panel to retain the second portion of the each panel to the first portion of the each panel. At step 1206, this pressing causes the adhesive to engage the filament, thereby retaining the filament between the first portion of the each panel and the second portion of the each panel. At step 1207, the method includes separating each panel from the adjoining panels by applying a force pulling each panel away from the adjoining panels, thereby tearing the perforation.

Figure 13:
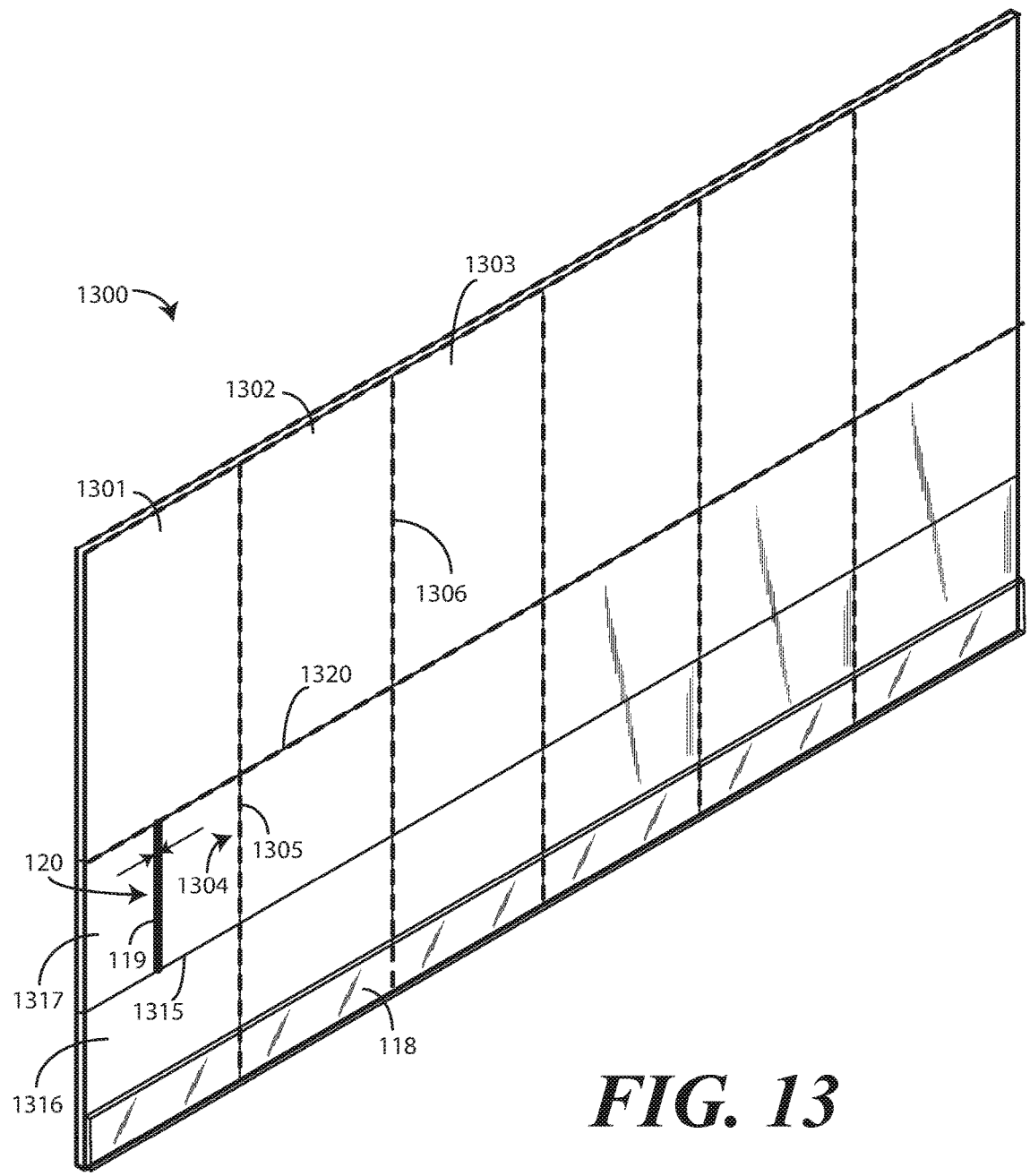
FIG. 13 illustrates another a perspective view of another explanatory sheet layer in accordance with one or more embodiments of the disclosure.
Figure 14:
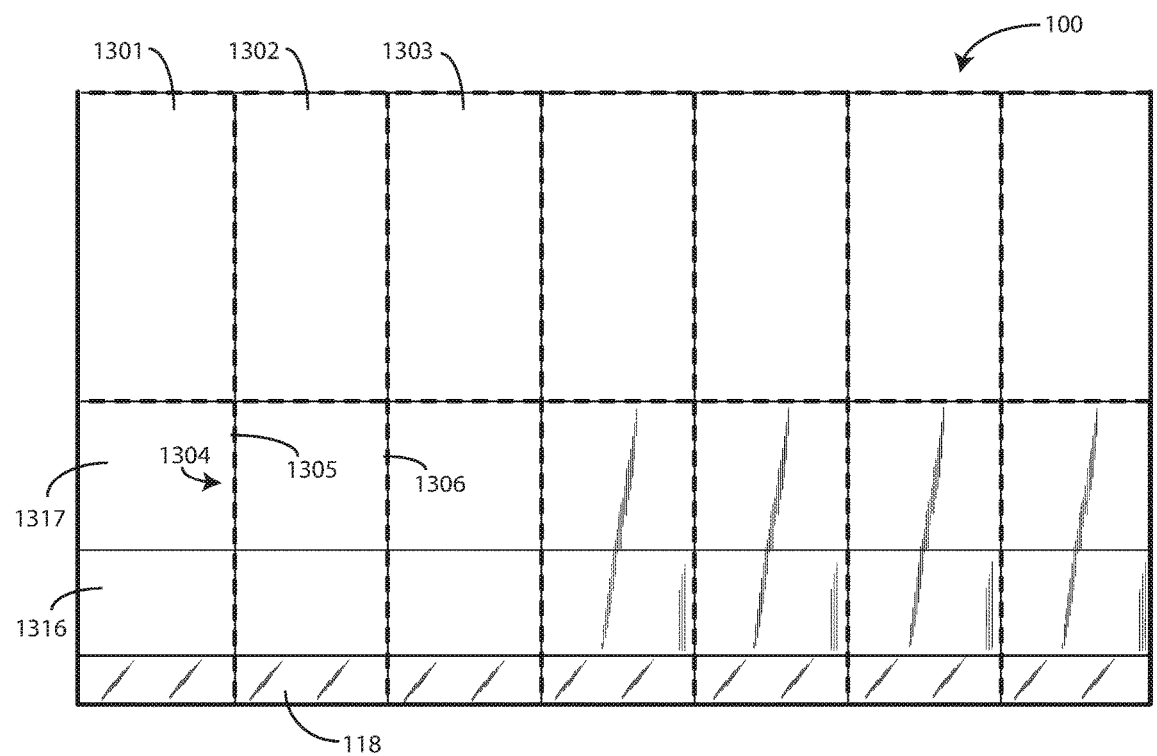
FIG. 14 illustrates a front elevation view of another explanatory sheet layer in accordance with one or more embodiments of the disclosure.

Turning now to FIGS. 13-14, illustrated therein is another explanatory sheet layer 1300 configured in accordance with one or more embodiments of the disclosure. FIG. 13 illustrates a perspective view of the sheet layer 1300, while FIG. 14 is a front elevation view of the same. In one or more embodiments, the sheet layer 1300 is manufactured from a paper-based material, such as stock paper, paperboard, cardboard, or baseboard. In other embodiments, the sheet layer 1300 is manufactured from a thermoplastic material, such as polyester, polyethylene, polypropylene, nylon, or composite materials. Other materials suitable for manufacturing the sheet layer 1300 will be obvious to those of ordinary skill in the art having the benefit if the disclosure. The sheet layer 1300 can have printing thereon, such as use instructions and/or branding information.

In one or more embodiments, the sheet layer 1300 defines one or more panels 1301,1302,103. In one or more embodiments, each panel 1301 is connected to at least one other panel 1302 along a common edge 1304. In one or more embodiments, a perforation 1305 extends along the common edge 1304, thereby defining a separation location between each panel 1301,1302,1303 to facilitate separation of the panel 1301 from the adjoining panel 1302 or panels. Illustrating by example, panel 1302 could be separated from panel 1301 and panel 1303 via perforations 1305,1306.

Each perforation 1305,1306 comprises a series of scores or cuts through the sheet layer 1300, while leaving interspaced portions of the sheet layer 1300 intact. Each perforation 1305,1306 allows panels to be separated from adjacent panels when an applied force pulls the panel away from its adjacent panels. Illustrating by example, applying a force to panel 1301 to the right and out of the page, as viewed in FIG. 1, while retaining panel 1302 in its location, or alternatively applying another force to panel 1302 to the left and into the page would cause panel 1301 to separate from panel 1302 in one or more embodiments.

In one or more embodiments, each perforation 1305,1306 comprises a score line that allows the sheet layer 100 to more easily be torn. Said differently, in one embodiment the perforation 1305,1306 is configured to tear and/or split when the one panel 1301 is pulled away from an adjoining panel 1302. This will be shown in more detail in subsequent figures. When this occurs, the tearing of the perforations 1305,1306 results in a splitting of the sheet layer 1300. The splitting or tearing can cause the panels 1301,1302 to separate at the common edge 1304. Panels can therefore be separated from the sheet layer 1300 simply tearing the desired panel away from the sheet layer 1300.

In one or more embodiments, a score line 1315 defines a partial incision into the sheet layer 1300. In the illustrative embodiment of FIGS. 13-14, the score line 1315 passes across each each panel 1301,1302,1303 at a quarter of the height of the panel 1301,1302,1303, thereby leaving three quarters of each panel 1301,1302,1303 above the score line 1315, and one quarter of each panel 1301,1302,1303 below the score line 1315. For example, in this illustrative embodiment the score line 1315 bisects panel 1301 into a first portion 1316 and a second portion 1317, whit the second portion 1317 having three times the surface area as the first portion 1316. Additionally, in this embodiment the score line 1315 is oriented substantially orthogonally with the perforations 1305,1306.

In this illustrative embodiment, the first portion 1316 and the second portion 1317 are rectangular in shape. However, where the score line 1315 is not a straight line, but is rather curved, piecewise linear, or takes other shapes, the first portion 1316 and the second portion 1317 of each panel 1301,1302,103 can take other shapes as well. In this illustrative embodiment, the first portion 1316 is smaller in size than the second portion 1317.

As before, the score line 1315 allows the first portion 136 of each panel 1301,1302,1303 to fold about the score line 1315. When the first portion 1316 of each panel 1301,1302,1303 is fully folded about the score line 1315, it will have a major face that abuts another major face of the second portion 1317. Accordingly, in one or more embodiments folding the first portion 1316 about the score line 1315 results in the first portion 1316 abutting the second portion 1317.

In one or more embodiments, and adhesive is disposed along the first portion 1316 of each panel 1301,1302,1303. In the embodiment of FIGS. 13-14, the adhesive (shown in FIG. 15) is disposed beneath a cover layer 118. The cover layer 118 is applied over the adhesive, and is removable to expose the adhesive. In one or more embodiments, this removal of the cover layer 118 occurs prior to any folding of the first portion 1316 and/or the second portion 1317 about the score line 1315.

In one or more embodiments, each panel 1301,1302,1303 can include an aligner 119 In this illustrative embodiment, the aligner 119 is centrally disposed along the second portion 1317.

In this embodiment, the aligner 119 comprises a line and a pair of arrows indicating a predefined location 120 for the filament. In other embodiments, the aligner 119 may be a dashed line or a rectangle indicating the predefined location 120 for the filament. Other types of aligners 119 will be obvious to those of ordinary skill in the art having the benefit of this disclosure.

In this illustrative embodiment, a medial perforation 1320 bisects the sheet layer 1300 by passing across the middle of the sheet layer 1300. In this illustrative embodiment, the medial perforation 1320 is orthogonal with the perforations 1305,1306 defining each panel 1301,1302,1303.

Figure 15:
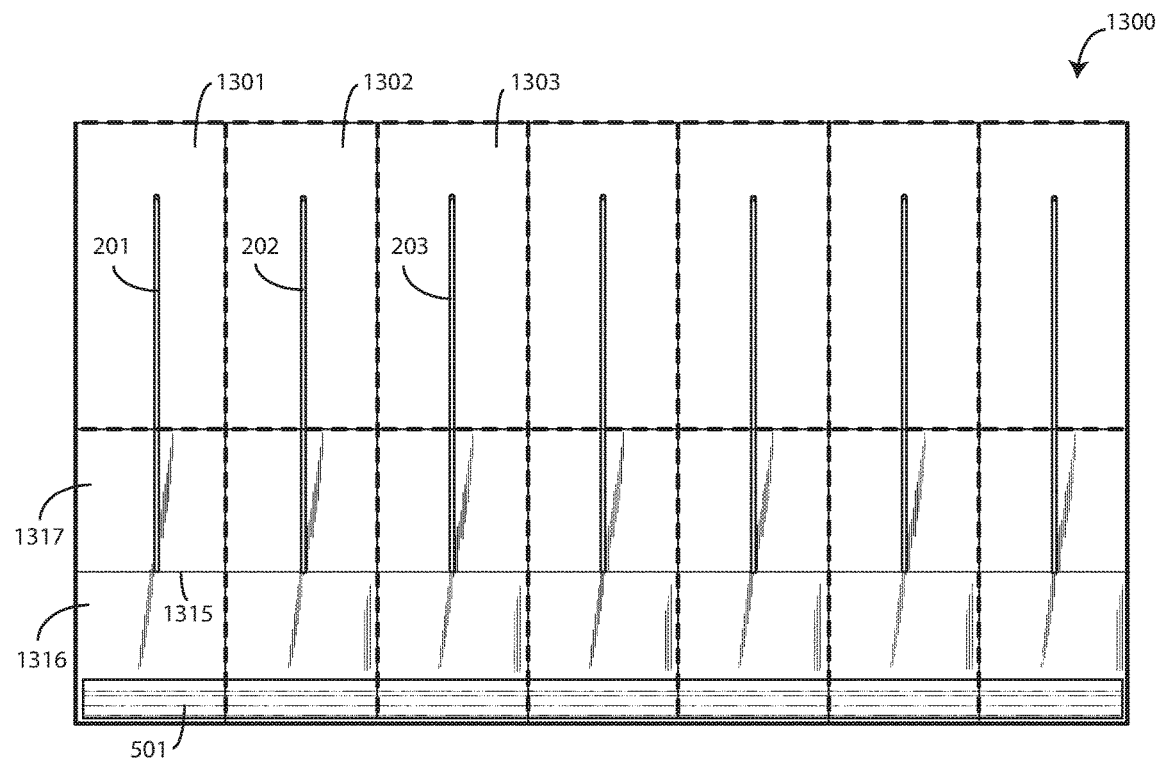
FIG. 15 illustrates a front elevation view of another partial assembly in accordance with one or more embodiments of the disclosure.

Turning now to FIG. 15, illustrated therein is the sheet layer 1300 of FIGS. 13-14. As shown, a filament 201,202, 203 has been placed on each panel 1301,1302,1303. In this illustrative embodiment, the filament 201,202,203 is situated along the second portion 1317 of each panel 1301,1302, 1303. In this illustrative embodiment, the filament 201,202, 203 extends from the score line 1315 initially across the second portion 1317 of the each panel 1301,1302,1303. In this illustrative embodiment, the filament 201,202,203 is shorter than the second portion 1317 of the each panel 1301,1302,1303.

In one or more embodiments, each filament 201,202,203 is a plastic filament. In other embodiments, each filament 201,202,203 is a nylon filament. Each filament 201,202,203 can have a predefined length, such as between two and two and one half inches. In one or more embodiments, each filament 201,202,203 has a diameter of about 0.0175 inches, although other diameters and lengths will be obvious to those of ordinary skill in the art having the benefit of this disclosure.

Figure 16:
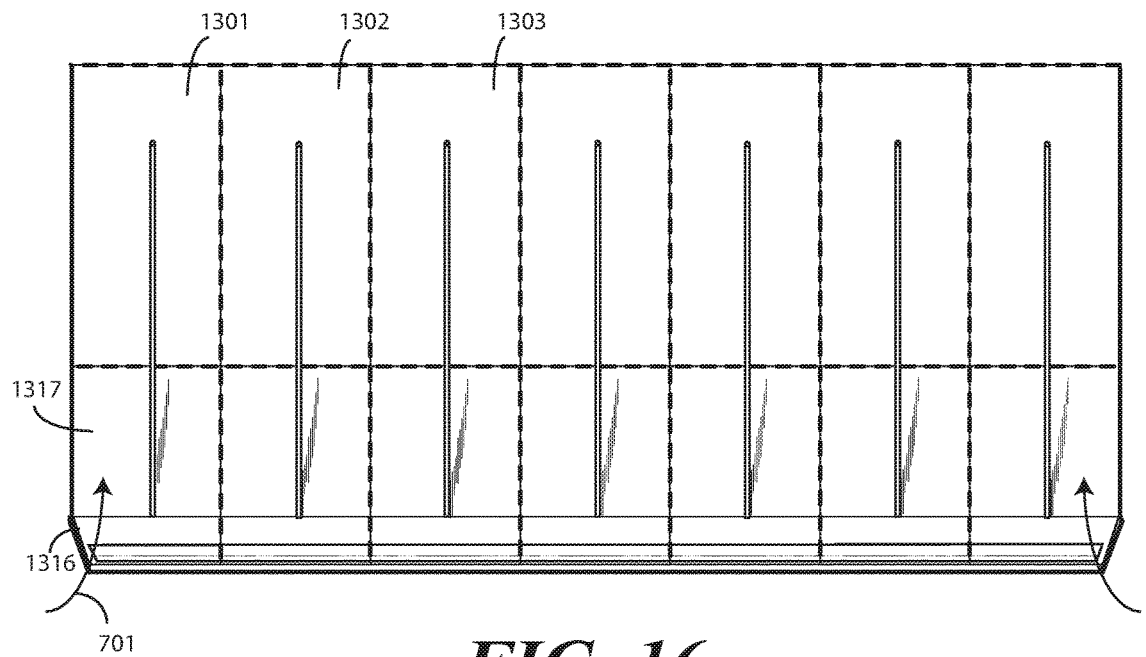
FIG. 16 illustrates one or more method steps in accordance with one or more embodiments of the disclosure.

As shown in FIG. 15, the cover layer (118) applied over the adhesive 501 has been removed, thereby exposing the adhesive 501. Turning now to FIG. 16, the first portion 1316 of each panel 1301,1302,1303 is then folded 701 about the score line 1315 toward the second portion 1317 of each panel 101,1302,1303. This folding 701 continues until a major face of the first portion 1316 of each panel 1301, 1302,103 abuts a major face of the second portion 1317 of each panel 1301,1302,1303, as shown in FIG. 17.

Figure 17:
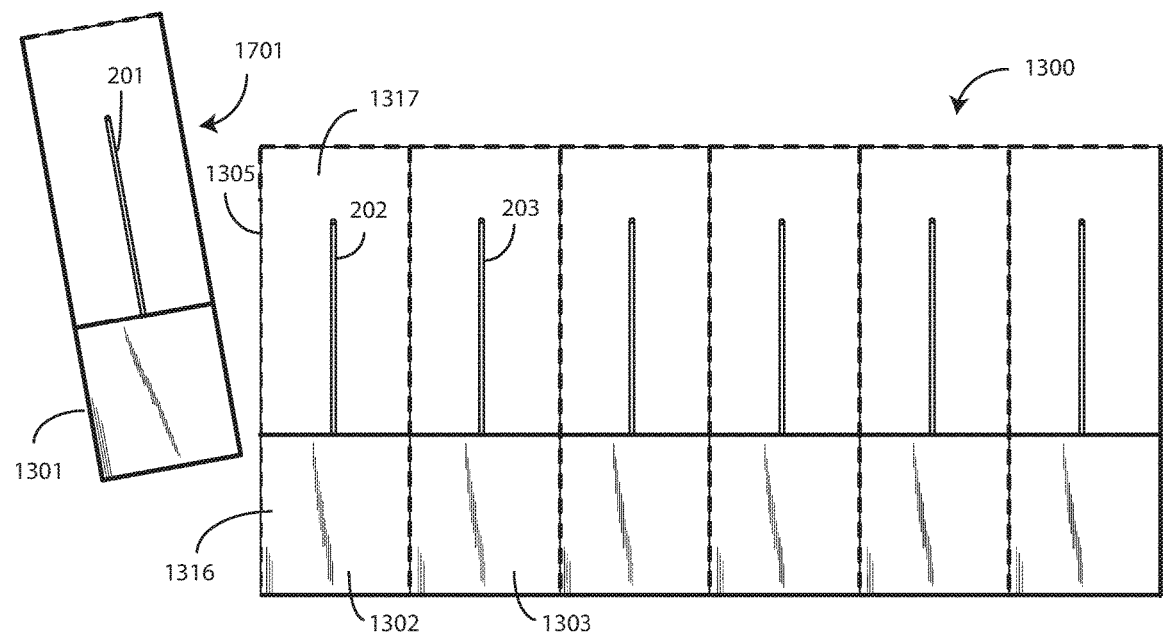
FIG. 17 illustrates one or more method steps in accordance with one or more embodiments of the disclosure.

Turning now to FIG. 17, pressing the first portion 1316 of each panel 1301,1302,1303 against the abutting major face of the second portion 1317 of each panel 1301,1302,1303 causes the adhesive (501) to retain the first portion 1316 to the second portion 1317 when the first portion 1316 and the second portion 1317 abut. Since the filament 201,202,203 is disposed between the first portion 1316 and the second portion 1317 of each panel as shown in FIG. 17, the adhesive (501) also retains the filament 201,202,203 between the first portion 1316 and the second portion 1317 of each panel 1301,1302,1303.

Since the filament 201,202,203 was placed with an end aligned with the score line (115) as shown in FIG. 15, this results in the filament 201,202,203 extending initially from the score line (115), then across the first portion 1316 and the second portion 1317. However, since the second portion 1317 is longer than the filament 201,202,203, each filament does not extend distally away from the second portion 1317. Instead, the second portion 1317 extends distally away from each filament 201,202,203.

A completed device 1701 can be separated from adjoining devices on the sheet layer 1300 by tearing the perforation 1305 defining the separation location between the panels 1301,1302,1303. Once each device 1701 has been separated from adjoining devices, it can be packaged as previously described.

Figure 18:
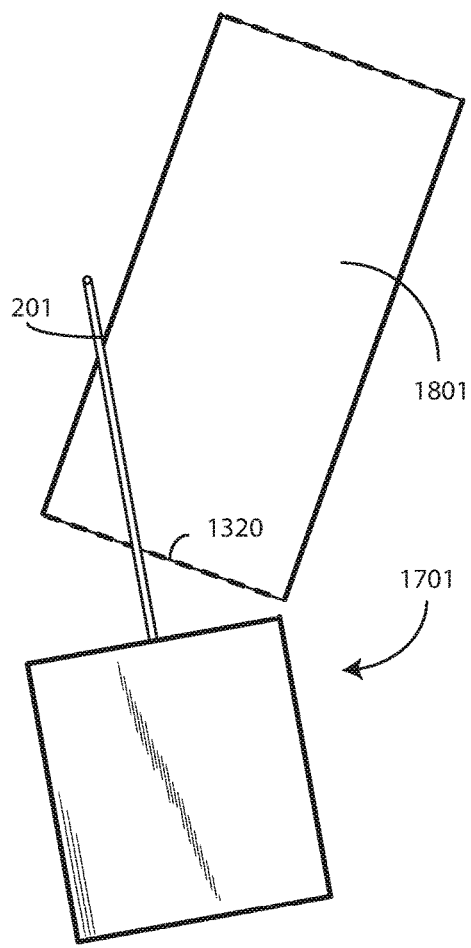
FIG. 18 illustrates one or more method steps in accordance with one or more embodiments of the disclosure.
Figure 19:
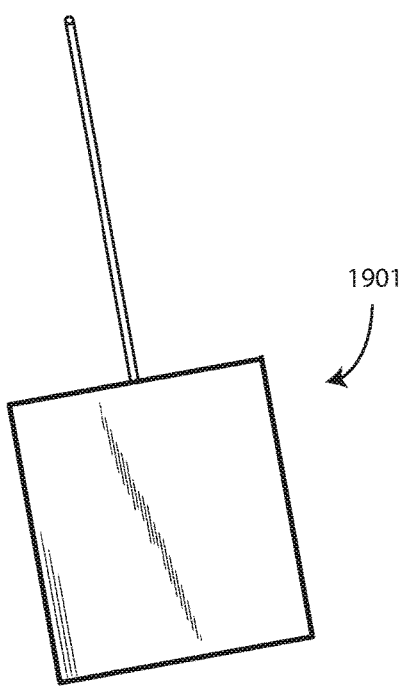
FIG. 19 illustrates an explanatory medical tool in accordance with one or more embodiments of the disclosure.

As shown in FIG. 18, prior to using the device 1701, a user would remove the upper section 1801 of the second portion (1317) by tearing the medial perforation 1320. Leaving the upper section 1801 of the second portion (1317) intact until use provides a mechanical support ensuring that the filament 201 does not get bent or damaged. The resulting ready for use device 1901 is shown in FIG. 19.

Figure 20:
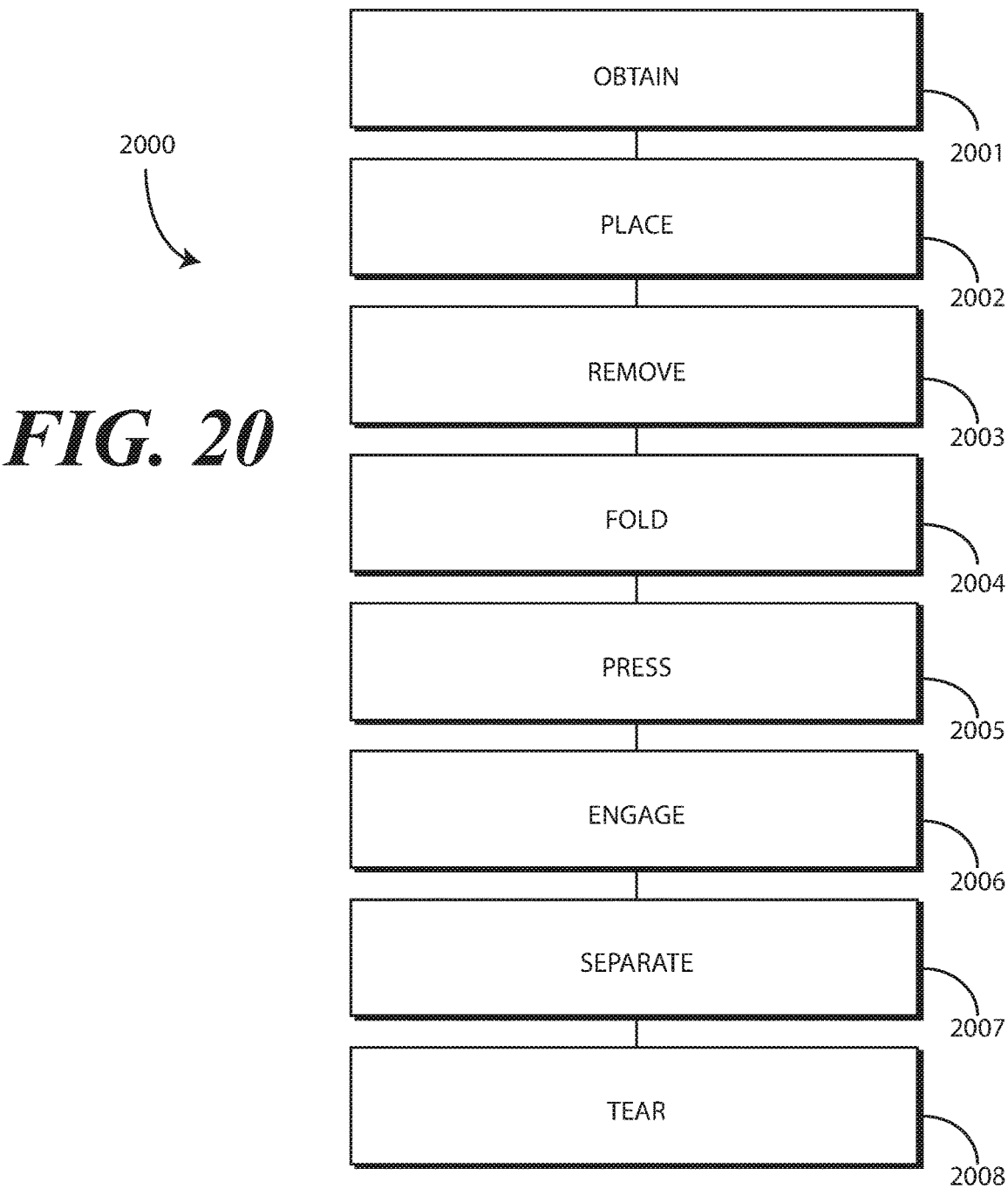
FIG. 20 illustrates another method in accordance with one or more embodiments of the disclosure.

Turning now to FIG. 20, illustrated therein is one explanatory method 2000 of manufacturing a device in accordance with one or more embodiments of the disclosure. At step 2001, the method 2000 includes obtaining a sheet layer. In one embodiment, the sheet layer defines a plurality of panels. In one embodiment, each panel is connected to at least one other panel along a common edge. In one embodiment, a perforation extends along the common edge. Where included, the perforation defines a separation location between each panel and its adjoining panels. In one or more embodiments, the sheet layer includes a medial perforation that is orthogonal with the perforations defining the separation location between each panel.

At step 2002, the method 2000 includes placing a filament along a first portion of the each panel. In one or more embodiments, the first portion comprises an aligner indicating a predefined location for the filament. Where this is true, step 2002 can include placing the filament on the aligner.

At optional step 2003, the method 2000 includes removing a cover layer from an adhesive disposed along a portion of each panel. At step 2004, the method 2000 includes folding a second portion of the each panel about a score line disposed between an edge of each panel and the medial perforation. In one or more embodiments, the score line is parallel to the medial perforation and is oriented orthogonally with the perforations defining the panels. Folding causes the first portion of the each panel and the second portion of the each panel to abut.

At step 2005, the method includes pressing the first portion of each panel against the second portion of each panel. In one or more embodiments, this pressing causes an adhesive attached to the second portion of the each panel to retain the second portion of the each panel to the first portion of the each panel. At step 2006, this pressing causes the adhesive to engage the filament, thereby retaining the filament between the first portion of the each panel and the second portion of the each panel. At step 2007, the method includes separating each panel from the adjoining panels by applying a force pulling each panel away from the adjoining panels, thereby tearing the perforation. At step 2008, prior to use, the medial perforation is torn, thereby removing the upper section of the second portion.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims.

What is claimed is:

1. A device, comprising:
   a sheet layer defining a plurality of panels, each panel connected to at least one other panel along a common edge;
   a perforation extending along the common edge, the perforation defining a separation location between the each panel and the at least one other panel allowing the each panel to be separated from the at least one other panel when an applied force pulls the each panel away from the at least one other panel;
   a score line defining a partial incision in the sheet layer, the score line passing across the each panel and oriented orthogonally with the perforation, the score line allowing a first portion of the each panel to fold about the score line to abut a second portion of the each panel;
   a medial perforation extending across the second portion and oriented parallel with the score line; and
   an adhesive, disposed along the first portion, the adhesive retaining the first portion of the each panel to the second portion of the each panel when the first portion and the second portion abut.

2. The device of claim 1, further comprising a filament disposed between the first portion and the second portion and extending across the medial perforation.

3. The device of claim 2, the filament shorter than the second portion.

4. The device of claim 3, the filament extending distally away from the first portion and the second portion by a distance of between one and two inches after the medial perforation is torn.

5. The device of claim 3, the adhesive retaining the filament between the first portion and the second portion.

6. The device of claim 4, further comprising and cover layer applied over the adhesive, the cover layer removable to expose the adhesive prior to folding the first portion about the score line.

7. The device of claim 6, the each panel coupled to at least two other panels, further comprising another perforation oriented orthogonally with the perforation, wherein a first panel, a second panel, and a third panel connect at an intersection of the perforation and the another perforation.

8. The device of claim 7, wherein the sheet layer is manufactured from cardboard.

9. The device of claim 8, wherein the first portion and the second portion are rectangular.

10. The device of claim 9, wherein the second portion comprises an aligner indicating a predefined location for the filament.

11. The device of claim 10, wherein the aligner is centrally disposed on the second portion.

12. A method of making a device, the method comprising:
    obtaining a sheet layer defining a plurality of panels, each panel connected to at least one other panel along a common edge, wherein a perforation extends along the common edge, thereby defining a separation location between the each panel and the at least one other panel;
    placing a filament along a first portion of the each panel;
    folding a second portion of the each panel about a score line bisecting the each panel and oriented orthogonally with the perforation to cause the first portion of the each panel and the second portion of the each panel to abut wherein the second portion is longer than the filament, with the filament extending from the score line across only some of the second portion to a distal end of the filament, with the second portion extending distally away from the distal end of the filament; and
    separating the each panel from the at least one other panel by applying a force pulling the each panel away from the at least one other panel by tearing the perforation.

13. The method of claim 12, further comprising pressing the first portion of the each panel against the second portion of the each panel, thereby causing an adhesive attached to the second portion of the each panel to retain the second portion of the each panel to the first portion of the each panel.

14. The method of claim 13, wherein the pressing causes the adhesive to engage the filament, thereby retaining the filament between the first portion of the each panel and the second portion of the each panel.

15. The method of claim 14, further comprising removing a cover layer from the adhesive prior to the folding the second portion of the each panel about the score line.

16. The method of claim 15, wherein the first portion of the each panel comprises an aligner indicating a predefined location for the filament, wherein the placing comprises placing the filament on the aligner.

17. A device, comprising:
    a first panel and a second panel connected together at a common edge;
    a perforation extending along the common edge, the perforation defining a separation location between the first panel and the second panel allowing the first panel to be separated from the second panel when an applied force pulls the first panel from the second panel;
    a score line defining a partial incision in the first panel, the score line bisecting the first panel and oriented orthogonally with the perforation, the score line allowing a first portion of the first panel to fold about the score line to abut a second portion of the first panel; and
    an adhesive, disposed along the first portion of the first panel, the adhesive retaining the first portion of the first panel to the second portion of the first panel when the first portion and the second portion are folded about the score line with the first portion retained at the score line to the second portion and where the first portion and the second portion abut.

18. The device of claim 17, the score line also bisecting the second panel.

19. The device of claim 18, further comprising a filament situated along the second portion of the first panel.

20. The device of claim 19, the filament extending from the score line initially across the second portion of the first panel, wherein the adhesive retains the filament against the second portion when the first portion and the second portion abut.

* * * * *